US011670420B2

(12) United States Patent
Ling et al.

(10) Patent No.: US 11,670,420 B2
(45) Date of Patent: Jun. 6, 2023

(54) DRAWING CONCLUSIONS FROM FREE FORM TEXTS WITH DEEP REINFORCEMENT LEARNING

(71) Applicant: KONINKLIJKE PHILIPS N.V., Eindhoven (NL)

(72) Inventors: Yuan Ling, Somerville, MA (US); Sheikh Sadid Al Hasan, Cambridge, MA (US); Oladimeji Feyisetan Farri, Yorktown Heights, NY (US); Vivek Varma Datla, Ashland, MA (US); Junyi Liu, Windham, NH (US)

(73) Assignee: Koninklijke Philips N.V., Eindhoven (NL)

( * ) Notice: Subject to any disclaimer, the term of this patent is extended or adjusted under 35 U.S.C. 154(b) by 624 days.

(21) Appl. No.: 16/491,489

(22) PCT Filed: Apr. 3, 2018

(86) PCT No.: PCT/EP2018/058388
§ 371 (c)(1),
(2) Date: Sep. 5, 2019

(87) PCT Pub. No.: WO2018/188981
PCT Pub. Date: Oct. 18, 2018

(65) Prior Publication Data
US 2020/0027560 A1     Jan. 23, 2020

Related U.S. Application Data

(60) Provisional application No. 62/621,142, filed on Jan. 24, 2018, provisional application No. 62/484,602, filed on Apr. 12, 2017.

(51) Int. Cl.
*G16H 10/60*     (2018.01)
*G16H 15/00*     (2018.01)
(Continued)

(52) U.S. Cl.
CPC ........... *G16H 50/20* (2018.01); *G06F 40/279* (2020.01); *G06F 40/30* (2020.01); *G06N 20/00* (2019.01); *G16H 10/60* (2018.01); *G16H 15/00* (2018.01)

(58) Field of Classification Search
CPC ........ G16H 50/20; G16H 10/60; G16H 15/00; G06N 20/00; G06N 99/00; G06N 5/04;
(Continued)

(56) References Cited

U.S. PATENT DOCUMENTS 8,554,707 B2   10/2013   Schafer et al.
8,775,341 B1   7/2014   Commons
(Continued)

OTHER PUBLICATIONS

Suresh et al. "Text Categorization Using Q-learning Algorithm", https://citeseerx.ist.psu.edu/viewdoc/download?doi=10.1.1.300.6378 &rep=rep1&type=pdf (Year: 2011).*
(Continued)

*Primary Examiner* — Fonya M Long
*Assistant Examiner* — Alaaeldin M Elshaer (57) ABSTRACT

Techniques are described herein for drawing conclusions using free form texts and external resources. In various embodiments, free form input data (202) may be segmented (504) into a plurality of input data segments. A first input data segment may be compared (510) with an external resource (304) to identify a first candidate conclusion. A reinforcement learning trained agent (310) may be applied (512) to make a first determination of whether to accept or reject the first candidate conclusion. Similar actions may be performed with a second input data segment to make a second determination of whether to accept or reject a second candidate conclusion. A final conclusion may be presented (522) based on the first and second determinations of the reinforcement learning trained agent with respect to at least
(Continued)

the first candidate conclusion and the second candidate conclusion.

7 Claims, 5 Drawing Sheets

(51) Int. Cl.
*G16H 50/20* (2018.01)
*G06N 20/00* (2019.01)
*G06F 40/279* (2020.01)
*G06F 40/30* (2020.01)

(58) Field of Classification Search
CPC ... G06N 3/04; G06N 7/00; G06N 3/08; G06F 40/279; G06F 40/30; G06F 17/27; G06F 17/24; G10L 15/16; H04N 19/52; G06Q 10/10
USPC .......................................................... 705/2, 3
See application file for complete search history.

(56) References Cited

U.S. PATENT DOCUMENTS

| | | | |
|---|---|---|---|
| 9,552,548 | B1 | 1/2017 | Brestoff |
| 2017/0116497 | A1 | 4/2017 | Georgescu et al. |
| 2018/0046764 | A1* | 2/2018 | Katwala ................. G16H 15/00 |

OTHER PUBLICATIONS

Narasimhan et al. "Language Understanding for Text-based Games using Deep Reinforcement Learning", https://arxiv.org/abs/1506.08941 (Year: 2015).*
Henss et al. "A Reinforcement Learning Approach for Adaptive Single- and Multi-Document Summarization", https://sis.h-da.de/fileadmin/Dokumente/Studiengaenge/IW/Lehrende/Margot_Mieskes/summarizationGSCL.pdf (Year: 2015).*
Suresh, S.R. et al., "Text Categorization Using Q-Learning Algorithm", Indian Journal of Computer Science and Engineering (IJCSE), 2011, pp. 315-324.
Henss, S. et al., "A Reinforcement Learning Approach for Adaptive Single-and Multi-Document Summarization", Proceedings of the Int. Conference of the German Society for Computational Linguistics and Language Technology, 2015, Section 3.
Narasimhan, K. et al., "Language understanding for text-based games using deep reinforcement learning", Proceedings of the 2015 Conference on Empirical Methods in Natural Language Processing (EMNLP'15), Sep. 17, 2015, pp. 1-11.
Mnih, V. et al., "Human-level control through deep reinforcement learning", Nature, vol. 518, No. 7540, Feb. 25, 2015, pp. 529-533.
El-Said, A.M. et al., "Exploiting Semantic Annotations and Q-Learning for Constructing an Efficient Hierarchy/Graph Texts Organization". Hindawi Publishing Corporation; Scientific World Journal;vol. 2015, Article ID 136172;http://dx.doi.org/10.1155/2015/136172.
Bayer, J. et al., "Pybrain". Journal of Machine Learning Research • Feb. 2010; DOI: 10.1145/1756006.1756030.
Goldberg, Y. et al., "Q-learning with censored data" The Annals of Statistics, 2012, vol. 40, No. 1, 529-560 DOI: 10.1214/12-AOS968.
International Search Report—PCT/EP2018/058388 dated Apr. 3, 2018.

* cited by examiner

DRAWING CONCLUSIONS FROM FREE FORM TEXTS WITH DEEP REINFORCEMENT LEARNING

CROSS-REFERENCE TO PRIOR APPLICATIONS

This application is the U.S. National Phase application under 35 U.S.C. § 371 of International Application No. PCT/EP2018/058388, filed on Apr. 3, 2018, which claims the benefit of U.S. Patent Application No. 62/621,142, filed on Jan. 24, 2018 and U.S. Patent Application No. 62/484,602, filed on Apr. 12, 2017. These applications are hereby incorporated by reference herein.

TECHNICAL FIELD

Embodiments described herein generally relate to artificial intelligence fields such as natural language processing, machine learning, and expert systems. More particularly but not exclusively, various embodiments relate to systems and methods for drawing correct conclusions, such as inferring correct diagnoses, using free form texts and external resources.

BACKGROUND

Clinical diagnosis is a critical and nontrivial aspect of patient care which often requires significant medical research and investigation based on an underlying clinical scenario. For example, given a clinical case narrative such as patient's past medical history and current condition, the clinician administers appropriate medical tests or procedures, performs complex cognitive processes to infer the probable diagnosis, and prescribes the best-possible treatment plan based on his/her experience or up-to-date knowledge obtained through substantial research on relevant external resources. Intelligent clinical decision support tools can support expert reasoning while dealing with complicated clinical scenarios to reduce the cognitive burden of clinicians during patient care.

Electronic health records ("EHRs"), and particularly free form clinical notes or reports are often unconstrained in nature. Rather, they constitute free form thoughts composed by the clinician. Consequently, for a given patient/diagnosis, different clinicians may compose free form clinical notes in entirely different ways. While earlier work built artificial intelligence ("AI") systems to support clinical support tools and decision making, they mostly used structured clinical data, such as physiological signals, vital signs, lab tests, and so forth. These models tend to lack the ability to capture the underlying uncertainties related to generating differential diagnoses and linguistic complexities of a clinical scenario as they consider medical codes and a finite number of diagnoses for prediction labels. As such, prior AI solutions are not well-suited for diagnoses inferencing using free form clinical notes.

For example, existing approaches for diagnosis inferencing mostly propose supervised classification models using various neural network architectures. However, such models heavily rely on large labeled data, and lack the ability to capture inherent ambiguities and complexities of a clinical scenario. Moreover, they are limited by the number of diagnosis labels and the use of medical codes to simplify the computational and linguistic difficulties of a clinical case. Other works have explored graph-based reasoning methods to incorporate relevant medical concepts and their associations. These approaches do not focus on the intuitive and analytical processes of a clinician to infer the probable diagnoses from a clinical case narrative.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

The present disclosure is directed to methods and apparatus for drawing correct conclusions, such as inferring correct diagnoses, using free form texts such as clinical notes and/or reports in combination with external reference resources. To overcome the sparsity in annotated data and adequate representation of ambiguities, the problem is formulated as a sequential decision-making process using deep reinforcement learning while leveraging external knowledge to infer the differential diagnoses. Unlike previous approaches, techniques described herein focus on the clinician's cognitive process to infer the most probable diagnoses from clinical narratives.

Given a clinical narrative (or a "free form clinical note"), a physician typically reviews the sentences sequentially, skipping those s/he deems irrelevant and focusing on those that would contribute to his/her understanding of the clinical scenario. While assimilating the sentences (i.e. understanding partial information), s/he tries to recognize a logical pattern or clinical progression similar to one or more prior patient encounters towards arriving at a candidate diagnosis. Ultimately, the intuition of the clinician is guided by understanding of these sentences and s/he can make an overall assessment of the scenario based on the narrative and/or additional evidence obtained from relevant external knowledge sources.

Techniques described herein simulate this cognitive flow by using a deep reinforcement learning technique. During training, an agent learns an optimal policy to obtain a final diagnoses through iterative search for candidate diagnoses from external knowledge sources via a sentence-by-sentence analysis of the inherent clinical context. In some embodiments, a deep Q-network architecture may be trained to optimize a reward function that measures the accuracy of candidate diagnoses. One model described herein predicts the differential diagnoses by utilizing the optimum policy learned to maximize the overall possible reward for an action during training.

Techniques described herein may enable a busy clinician considering relevant differential diagnoses that could otherwise be ignored due to inadvertent diagnostic errors. Also, nurse practitioners and other medical personnel can use techniques described herein as a source of second opinion before contacting a physician towards accurately diagnosing and managing their patients. And while examples described herein related to inferring medical diagnoses, this is not meant to be limiting. Techniques described herein may be applicable in a variety of other contexts in which conclusions can be drawn from free form narratives.

Generally, in one aspect, a method may include: segmenting free form input data into a plurality of input data segments; comparing a first input data segment of the plurality of input data segments with an external resource to identify a first candidate conclusion; applying a reinforcement learning trained agent to make a first determination of whether to accept or reject the first candidate conclusion; comparing a second input data segment of the plurality of input data segments with the external resource to identify a second candidate conclusion; applying the reinforcement learning trained agent to make a second determination of whether to accept or reject the second candidate conclusion; and presenting a final conclusion based on the first and second determinations of the reinforcement learning trained agent with respect to at least the first candidate conclusion and the second candidate conclusion.

In various embodiments, the free form input data may include one or more free form clinical notes, and the plurality of input data segments comprise a plurality of sentences contained in the one or more clinical notes. In various embodiments, the first and second candidate conclusions may include first and second candidate diagnoses, and the final conclusion comprises a final diagnosis.

In various embodiments, wherein the reinforcement learning trained agent may be a deep Q-network ("DQN") agent. In various embodiments, the reinforcement learning trained agent may be trained to accept or reject candidate conclusions based on a reward function. In various embodiments, the reward function may include an instant reward and a global reward.

In various embodiments, applying the reinforcement learning trained agent to make the first determination of whether to accept or reject the first candidate conclusion includes applying a state vector as input for the reinforcement learning trained agent. In various embodiments, the state vector encodes the first input data segment and the first candidate conclusion.

In addition, some implementations include one or more processors of one or more computing devices, where the one or more processors are operable to execute instructions stored in associated memory, and where the instructions are configured to cause performance of any of the aforementioned methods. Some implementations also include one or more non-transitory computer readable storage media storing computer instructions executable by one or more processors to perform any of the aforementioned methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

DETAILED DESCRIPTION

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein; rather, these embodiments are provided as part of a thorough and complete disclosure, to fully convey the scope of the concepts, techniques and implementations of the present disclosure to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices. Portions of the present disclosure include processes and instructions that may be embodied in software, firmware or hardware, and when embodied in software, may be downloaded to reside on and be operated from different platforms used by a variety of operating systems.

The present disclosure also relates to an apparatus for performing the operations herein. This apparatus may be specially constructed for the required purposes, or it may include a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each may be coupled to a computer system bus. Furthermore, the computers referred to in the specification may include a single processor or may be architectures employing multiple processor designs for increased computing capability.

The processes and displays presented herein are not inherently related to any particular computer or other apparatus. Various general-purpose systems may also be used with programs in accordance with the teachings herein, or it may prove convenient to construct more specialized apparatus to perform one or more method steps. The structure for a variety of these systems is discussed in the description below. In addition, any particular programming language that is sufficient for achieving the techniques and implementations of the present disclosure may be used.

In addition, the language used in the specification has been principally selected for readability and instructional purposes and may not have been selected to delineate or circumscribe the disclosed subject matter. Accordingly, the present disclosure is intended to be illustrative, and not limiting, of the scope of the concepts discussed herein.

Figure 1:
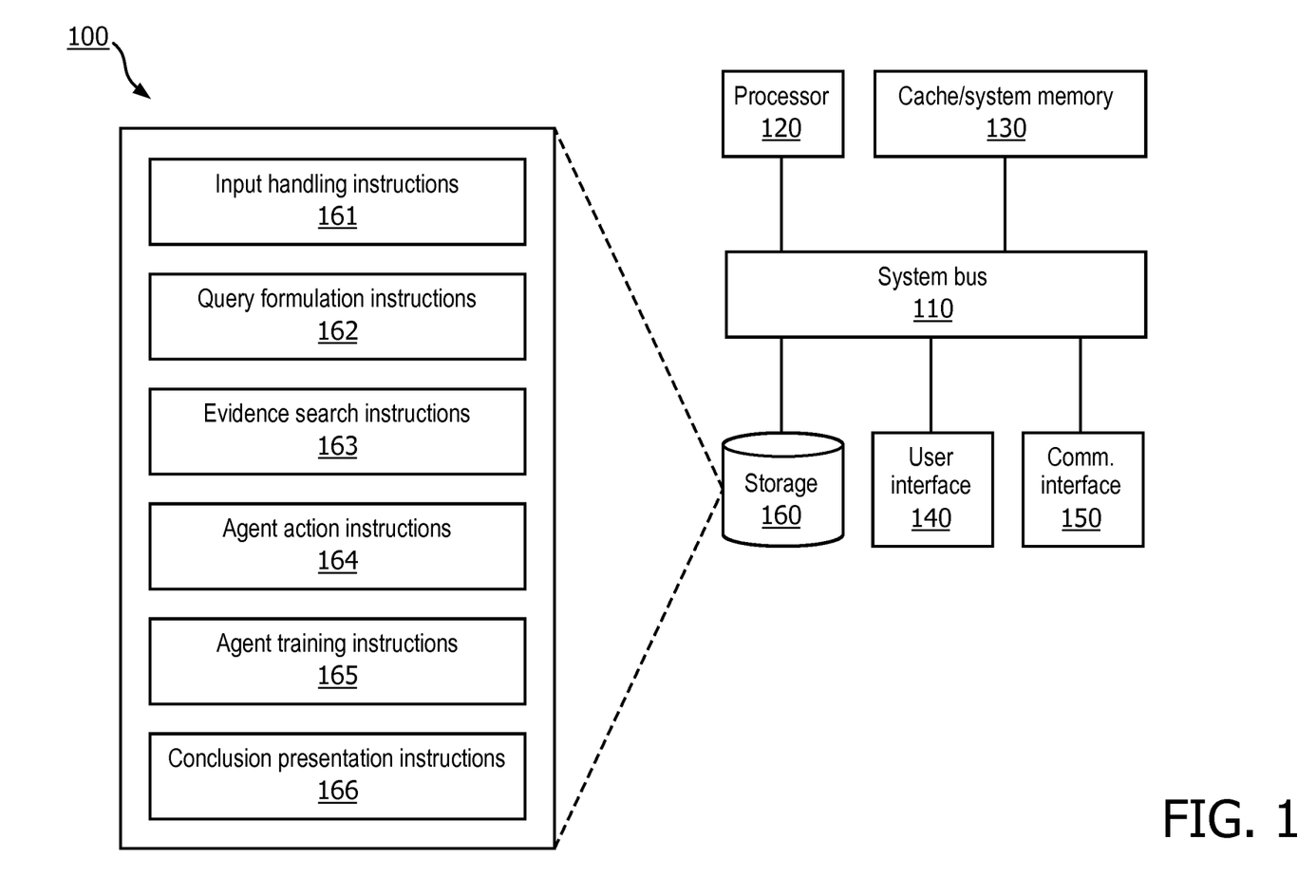
FIG. 1 illustrates an example environment in which selected aspects of the present disclosure may be implemented.

FIG. 1 illustrates a system 100 for inferring a patient's diagnosis in accordance with one embodiment. As shown, the system 100 includes a processor 120, memory 130, a user interface 140, a communication interface 150, and storage 160 interconnected via one or more system buses 110. It will be understood that FIG. 1 constitutes, in some respects, an abstraction and that the actual organization of the system 100 and the components thereof may differ from what is illustrated.

The processor 120 may be any hardware device capable of executing instructions stored on memory 130 or storage 160 or otherwise capable of processing data. As such, the processor 120 may include a microprocessor, field programmable gate array (FPGA), application-specific integrated circuit (ASIC), or other similar devices. The memory 130 may include various memories such as, for example L1, L2, or L3 cache or system memory. As such, the memory 130 may include static random access memory (SRAM), dynamic RAM (DRAM), flash memory, read only memory (ROM), or other similar memory devices.

The user interface 140 may include one or more devices for enabling communication with a user such as a patient or medical personnel. For example, the user interface 140 may include a display, a mouse, and a keyboard for receiving user commands. In some embodiments, the user interface 140 may include a command line interface or graphical user interface that may be presented to a remote terminal via the communication interface 150. In some embodiments, the user interface 140 may present an agent in the form of an agent (e.g., chatbot) to communicate with a user audibly and/or visually. The presented agent may of course vary and depend on the application.

The communication interface 150 may include one or more devices for enabling communication with other hardware devices. For example, the communication interface 150 may include a network interface card (NIC) configured to communicate according to the Ethernet protocol. Additionally, the communication interface 150 may implement a TCP/IP stack for communication according to the TCP/IP protocols. Various alternative or additional hardware or configurations for the communication interface 150 will be apparent.

The storage 160 may include one or more machine-readable storage media such as read-only memory (ROM), random-access memory (RAM), magnetic disk storage media, optical storage media, flash-memory devices, or similar storage media. In various embodiments, the storage 160 may store instructions for execution by the processor 120 or data upon with the processor 120 may operate.

For example, the storage 160 may include or otherwise be configured to execute various components for drawing conclusions from free form input. As seen in FIG. 1, these components may include input handling instructions 161, query formulation instructions 162, evidence search instructions 163, agent action instructions 164, agent training instructions 165, and conclusion presentation instructions 166. An example of the operation of these instructions will be described in greater detail below. As will be understood in the field of machine learning, the various instructions 161-166 may be executed at different times for different purposes such as, for example, as part of a training phase and as an operation phase. For example, the agent training instructions 165 (which may include, e.g., a reward function and instructions for implementing Q-learning) may only be executed during the training phase to digest a large training set of clinical narratives and associated ground truths. As another example, the conclusion presentation instructions 166 may only be executed during the operation phase to output the inferred conclusion(s) to the user according to the purpose for which the system has been trained and deployed.

It will also be understood that in various embodiments, the training phase and operation phase may not be performed in the same location or by the same device. For example, the agent action instructions 164 (e.g., models associated therewith) may be trained in a lab setting, e.g., using agent training instructions 165, and then deployed across other hospital systems or on a cloud-based virtual machine accessible via, e.g., a mobile app, web browser, etc. Accordingly, in some embodiments, the system 100 may omit one or more of the instructions 161-166 such as, for example, the agent training instructions 165 or conclusion presentation instructions 166. Additionally, in some embodiments, one or more instructions 161-166 may be hosted on a different device. For example, the agent action instructions 164 may be hosted on a separate device (not shown) and the remaining instructions may utilize the agent action instructions 164 as a remote service, e.g., via a RESTful API.

It will also be understood that in some embodiments, the training phase and operation phase may at least partially overlap. For example, in some embodiments, the agent may continue to learn and improve (e.g., based on human operator feedback taken as the ground truth on a case-by-case basis) even after deployment.

In some embodiments, the device 100 may be implemented as a cloud-based virtual machine. As such, the various components 120-160 may, in some embodiments, be distributed across multiple physical devices and, in some cases, may be duplicated. For example, a virtual machine may utilize two or more processors 120 in various embodiments.

Figure 2:
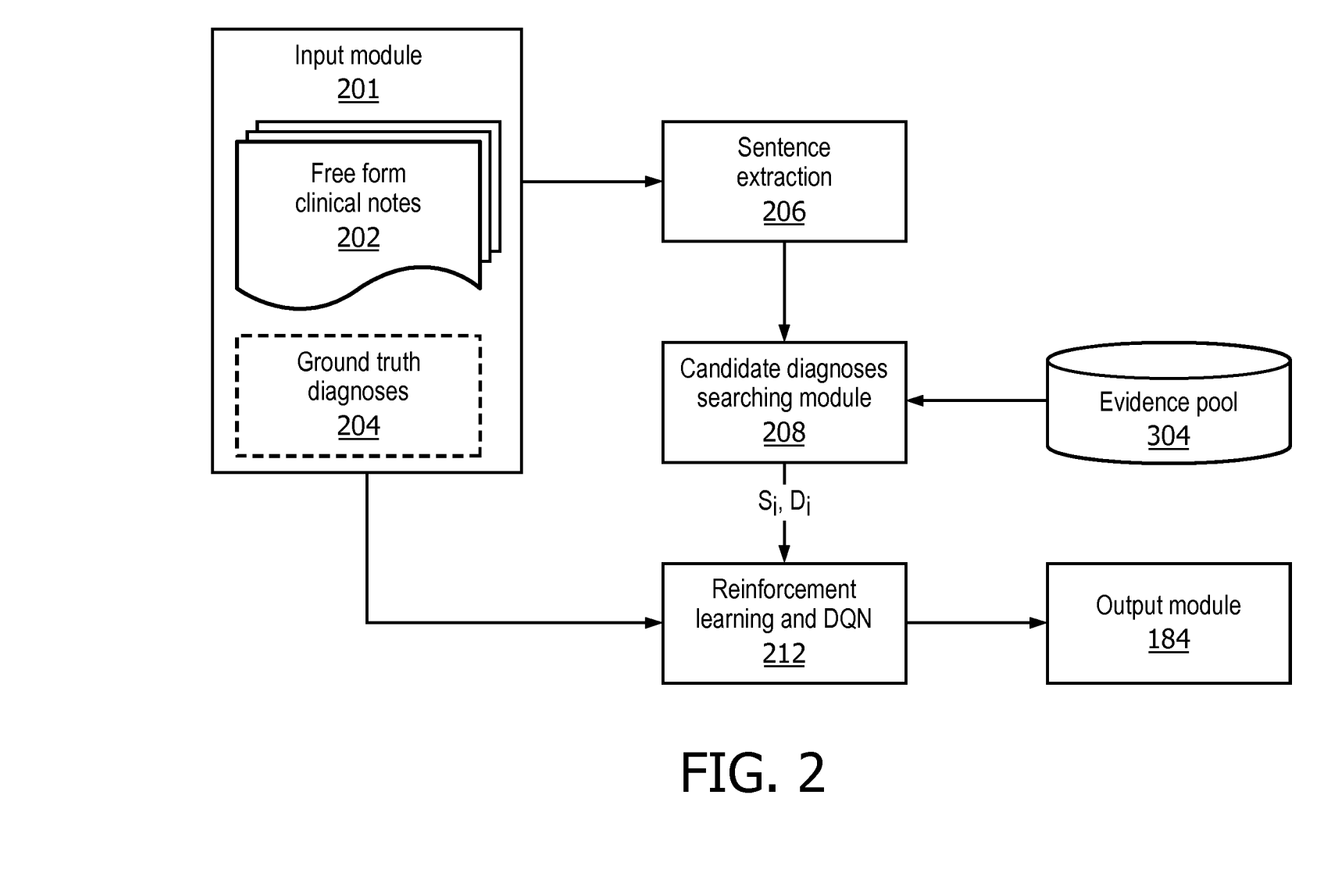
FIG. 2 schematically depicts, at a relatively high level, one example process flow architecture for implementation of selected aspects of the present disclosure.
Figure 3:
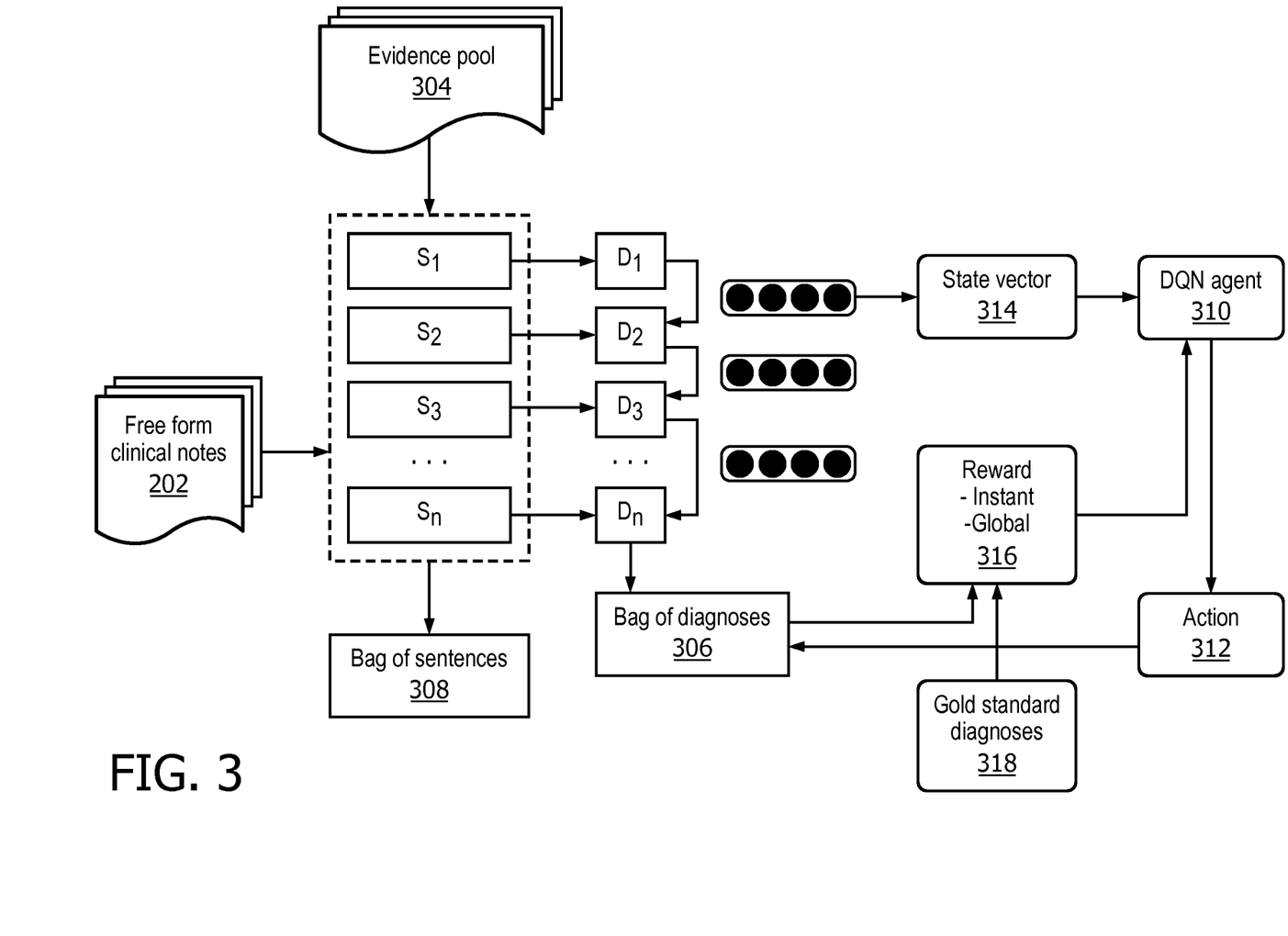
FIG. 3 schematically depicts, in slightly more detail than FIG. 2, one example process flow architecture for implementation of selected aspects of the present disclosure.

The query formulation instructions 162 may be executed to formulate one or more queries for external resources/evidence pool 304 (see FIGS. 2-3). The query formulation instructions 162 may formulate these queries based on pre-defined templates or dynamically using some heuristics (e.g., based on n-grams, all concepts, all text, etc.). For example, in some embodiments, the query formulation instructions 162 may simply form a Boolean query where each concept is joined by an AND or an OR operator. As another example, the query may be formed as an elasticsearch query. Various alternative methods for constructing queries based on textual or other types of concepts will be apparent.

The queries formulated by the query formulation instructions 162 may be executed against one or more external resources/evidence pool 304. In some embodiments, the external resources/evidence pool 304 may include remote databases or other collection of expert information such as, for example, Wikipedia, Mayo-Clinic, MIMIC, HumanDx, or the like. While the term "external resources" is used, it will be apparent that such term may encompass knowledge sources that are at least partially locally stored. For example, in some embodiments, the system may store a local cache of entries from such remote sources that may be queried. To execute the queries, the query formulation instructions 162 may also execute the queries by submitting the queries to a search engine via suitable application programming interface (APIs) such as those offered by the external resources (e.g., the built-in Wikipedia or Mayo Clinic search functionality) or by a third party service (e.g., search engines offered by Google or Bing to search the external resources). The evidence search instructions 163 may be executed to search the external resources/evidence pool 304 for relevant evidence with respect to the clinical scenario, e.g., using the query formulated using the query formulation instructions 162.

Agent action instructions 164 may be executed to make decisions about candidate conclusions and sentences examined during the conclusion inference process. As will be described in more detail below, in various embodiments, agent action instructions 164 may include instructions that employ one or more trained models, such as one or more artificial neural networks, support vector machines, etc., to draw conclusions from free form input. Agent training instructions 165 may be executed to train such models, as will be described below. Conclusion presentation instructions 166 may be executed to present one or more conclusions as output, e.g., audibly and/or visually.

FIG. 2 depicts, at a relatively high level, an overall architecture that may be employed to implement selected aspects of the present disclosure. An input module 201 may have access to free form input, such as free form clinical notes 202. In various embodiments, free-form clinical notes 202 may be composed by medical personnel when examining a patient and/or lab results and/or other data associated with a patient. In some embodiments, free-form clinical notes 202 may be associated with electronic health records ("EHRs") that are stored, for example, in one or more databases associated with a hospital information system (not depicted). Additionally, in some embodiments, particularly for training purposes, one or more of these free form clinical notes may include corresponding ground truth diagnoses 204, i.e. actual diagnoses of patients for which the free form clinical notes 202 were created.

Also depicted in FIG. 2 is a sentence extraction module 206. In this example, sentence extraction module may be configured, e.g., by way of input handling instructions 161, to extract individual sentences from free form clinical notes 202. More generally, in some embodiments, module 206 may be configured to extract input segments from free form input. These extracted sentences may be provided to a candidate diagnosis searching module 208, which may, for instance, be implemented using query formulation instructions 162 and/or evidence search instructions 163. Candidate diagnosis searching module 208 may be configured to identify one or more documents in an evidence pool 304 that most closely match (e.g., are most relevant to) a current sentence $S_i$. Various matching techniques may be employed, as were described previously with respect to query formulation instructions 162.

Each document matched by candidate diagnosis searching model 208 may include a corresponding conclusion. For example, in the diagnosis inference context, evidence pool 304 may include a corpus of clinical reference documents, each describing a particular health condition. These individual documents may include, for example, signs, symptoms, prognoses, diagnoses, etc. In some embodiments, the diagnosis associated with each clinical reference document, which in some cases may be the document's title, t may be used as a candidate diagnosis (or more generally, a candidate conclusion).

In some embodiments, a sentence/candidate diagnosis pair, $S_i$, $D_i$, may be passed to a reinforcement learning and deep Q-network ("DQN") module 212. Module 212 may be configured (i.e. previously trained) to determine whether, for each sentence/candidate diagnosis pair, $S_i$, $D_i$, the candidate diagnosis $D_i$ should be accepted or rejected. Additionally or alternatively, in some embodiments, module 212 may be configured to determine whether, for each sentence/candidate diagnosis pair, $S_i$, $D_i$, the sentence $S_i$ should be accepted or rejected.

The system of FIG. 2 may increment (or take "turns") through each sentence of free form clinical note 202 until no sentences remain. During these multiple increments, module 212 may accumulate candidate diagnoses and/or sentences that it accepts, while rejected diagnoses/sentences may be discarded. Once all sentences are processed, module 212 may provide, e.g., to an output module 214, the accumulated diagnoses and/or sentences. Output module 214 may execute conclusion presentation instructions 166 to provide output (e.g., visual, audio) that presents the remaining candidate diagnoses as likely diagnoses for a patient about which the input free form clinical note 202 was composed.

FIG. 3 depicts a more detailed view than FIG. 2 of an overall architecture that may be employed to implement techniques described herein. In various embodiments, input may take the form of free-form clinical notes 202 and one or more external resources that, as described previously, are referred to herein as an "evidence pool" 304. The following excerpt is an illustrative example of a free-form clinical note associated with a known diagnosis, pulmonary embolism:

An 87 yo woman with h/o osteoporosis, DM2, dementia, depression, and anxiety presents s/p fall with evidence of C2 fracture, chest pain, tachycardia, tachypnea, and low blood pressure.

As noted previously, evidence pool 304 may include a corpus of reference documents that may be used to draw conclusions from the input 102. For example, evidence pool 304 may include reference medical documents that describe various aspects of medical conditions, such as symptoms, prognosis, diagnosis, treatment, etc. The following excerpt is an illustrative example of a reference document associated with pulmonary embolisms:

> Symptoms of pulmonary embolism are typically sudden in onset and may include one or many of the following: dyspnea (shortness of breath), tachypnea (rapid breathing), chest pain of a "pleuritic" nature (worsened by breathing), cough and hemoptysis (coughing up blood).

In various embodiments, input data 202 may be broken or segmented into a plurality of input data segments, such as a plurality of sentences $S_{1-n}$. Each sentence $S_i$ may be compared, e.g., one after another in increments, with one or more documents in evidence pool 304 to identify one or more candidate conclusions, such as candidate diagnoses $D_{1-n}$. In some embodiments, deep reinforcement learning may be used to infer conclusions such as diagnoses from the candidate conclusions/diagnoses generated at each step. For example, at each iteration (i.e., for each sentence $S_i$), a trained agent 310, which in some embodiments may take the form of a deep Q-network agent, may take action 312 to determine whether to accept or reject one or more candidate diagnoses $D_i$. If the candidate diagnosis $D_i$ (or more generally, candidate conclusion) is accepted, it may be added to a bag of diagnoses 306. Otherwise it may be discarded.

After the last sentence $S_n$ is processed, bag of diagnoses 306 may include one or more diagnosis that are likely applicable to the patient associated with the free form clinical note 202. These one or more diagnoses (or more generally, one or more conclusions) may be presented as a final conclusion (or diagnosis) based on decisions of trained agent 310 with respect to the various candidate conclusions (e.g., candidate diagnoses $D_{1-n}$) that were not rejected. For example, audio and/or visual output may be presented via user interface 140 that indicates the patient's likely diagnosis.

Also depicted in FIG. 3 is a bag of sentences 308. In various embodiments, trained agent 310 may accept or reject the current sentence based on its influence in causing candidate diagnoses to be accepted and stored in bag of diagnoses 306. Consequently, bag of sentences 308 may, after processing of sentences $S_{1-n}$, contain one or more sentences that were most influential and/or important in providing the one or more diagnoses (or more generally, conclusions) contained in bag of diagnoses 306.

At each iteration, i.e. during processing of each sentence $S_i$, a state vector 314 may be generated. In various embodiments, state vector 314 may encode a confidence on the current sentence $S_i$ and a corresponding candidate diagnosis $D_i$. In some embodiments, a state vector 314 may be represented as a continuous real-valued vector containing the following information: 1) S1: similarity between the current sentence and bag-of sentences 308; 2) S2: similarity between the current sentence and the context of the input free form clinical note 202; 3) S3: similarity between the current sentence $S_i$ and the source article context of the current candidate diagnosis $D_i$; 4) S4: similarity between bag-of-sentences 308 and the source article context of the current candidate diagnosis $D_i$; 5) S5: similarity between the current candidate diagnosis $D_i$ and bag-of-diagnoses 306; and 6) the number of words in the current sentence $S_i$.

These similarities S1-5 may be computed using various techniques. In some embodiments, they may be computed using string similarity, which includes n-gram (unigram/bigram/trigram), and Levenshtein distance. Additionally or alternatively, in some embodiments, these similarities may be computed using similarity/distance measures that employ one-hot vector representations including Jaccard similarity, cosine similarity, Manhattan distance, Euclidean distance, and/or fractional distance.

In some embodiments, in addition to the above similarities S1-5, words in the current sentence $S_i$ (e.g., as a bag of words) may be encoded into the current state vector 314, e.g., using a Long Short Term Memory ("LSTM") network and mean pooling. For example, and referring to FIG. 4, in some embodiments the sequence of words $W_{1-m}$ in the current sentence may be provided as input. Their one-hot vector embeddings may be passed as input to LSTM cells $430_{1-m}$. Output of cells $430_{1-m}$ may be provided to a mean pooling layer 433. Output of the mean pooling layer 433 may take the form of a vector representation of the words, which may be combined (e.g., concatenated) with the similarities S1-5 (described above, depicted in FIG. 4 as a similarity vector 432) to produce current state vector 314. In some embodiments, the state vector 314 may be applied as input across a linear layer 434, which may include a machine learning model such as a feed-forward neural network having one or more hidden layers. Output of linear layer 434 may be provided as input to a rectifier (ReLU) layer 436 (or some other activation function, such as softmax), which may provide one or more actions to be performed by trained agent 310, such as a candidate diagnosis action 438 and a current sentence action 440.

Figure 4:
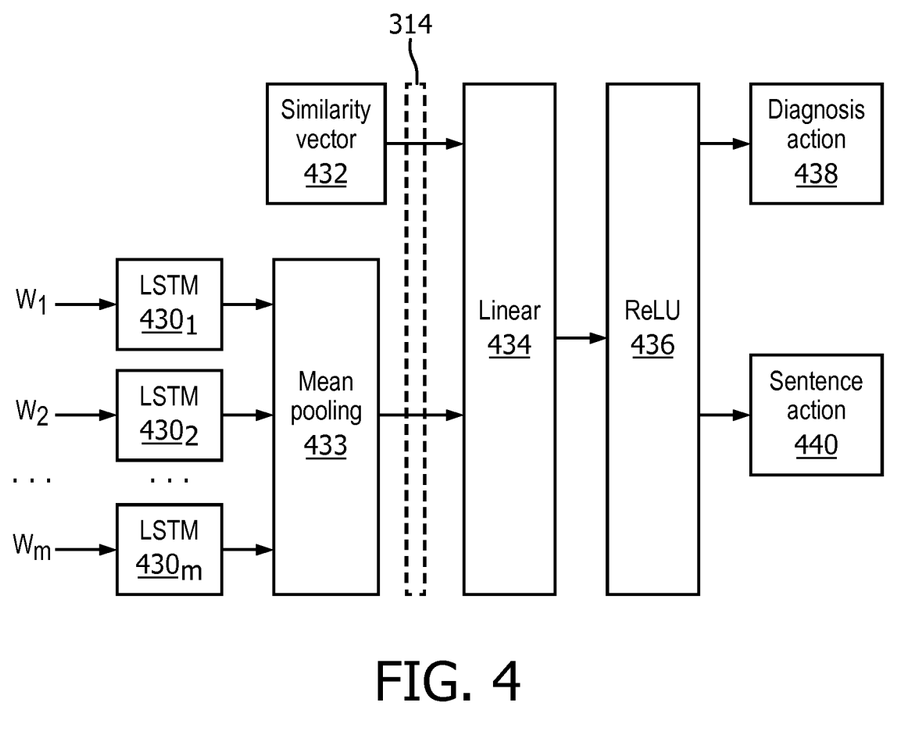
FIG. 4 schematically depicts an example of a trained agent architecture, in accordance with various embodiments.

Referring both to FIGS. 3 and 4, in various embodiments, at each iteration, trained agent 310 may take one or both of actions 438 and 440. Candidate diagnosis action 438 may include accepting one or more current candidate diagnoses $D_i$, rejecting one or more current candidate diagnoses $D_i$, rejecting all current candidate diagnoses $D_i$, and stop. Sentence action 440 may include accepting or rejecting the current sentence $S_i$.

In various embodiments, trained agent 310 may receive limited supervision from ground truth diagnoses via a reward function 316. In various embodiments, reward function 316 may be selected so that the accuracy of the final diagnosis prediction is maximized. There are two types of rewards that may be considered—instant reward ($r_{instant}$) and global reward ($r_{global}$). An overall reward r may in some embodiments be calculated using the following equation:

$$r = r_{instant} + r_{global} \qquad (1)$$

In some embodiments, $r_{instant}$ may be calculated based on the match of a candidate diagnosis $D_i$ with a gold standard diagnosis 318 in accordance with the following:

$$rinstant = \begin{cases} 1, & \text{if candidate diagnosis matches} \\ 0, & \text{otherwise} \end{cases} \qquad (2)$$

On the other hand, $r_{global}$ may be equal to the number of correct diagnoses in bag of diagnoses 306, minus the number of incorrect diagnoses in bag of diagnoses 306.

Trained agent 310 may be trained (e.g., ahead of time) in various ways, such as with Q-learning. However, it is impractical to maintain the Q-values for all possible state-action pairs. Consequently, in order to learn the Q-value approximated by trained agent 310, in some embodiments, iterative updates may be derived from the following equation (Bellman equation:

$$Q_{i+1} = E[r + \gamma \max_{a'} Q_i(s', a') | s, a] \qquad (3)$$

wherein $\gamma$ is a discount factor for the future rewards and the expectation is over the whole training process. In some embodiments, a deep Q-network ("DQN") architecture such as that depicted in FIG. 4 may be employed which approximates the Q-value function and predicts Q(s, a) for all possible actions. During training, the linear layer 434 has its weights modified using various machine learning techniques, such as back propagation and/or stochastic gradient descent, as part of learning Q-values for as many state-action pairs as possible.

In some embodiments, techniques described herein may be implemented as follows. Integration of external knowledge sources for clinical diagnosis inferencing may be modeled as a Markov Decision Process ("MDP"). At each MDP step/increment, trained agent 310 takes a sentence $S_i$ from the free form clinical note 202 and uses it as a query to obtain an external document from evidence pool 304 so that the sentence $S_i$ can be mapped to a candidate diagnosis $D_i$. As noted previously, evidence pool 304 contains external knowledge sources about medical conditions and/or diagnoses.

For each sentence $S_i$ and corresponding candidate diagnosis $D_i$, a state vector 314 (s) is created to encode their information. The state vector 314 may include information about the importance of the current sentence $S_i$ and current candidate diagnosis $D_i$ with respect to inferring the most probable diagnoses for the input free form clinical note 202. In a state s, trained agent 310 takes an action a to get to the next state, s'=s+a. The reward function r(s, a) described previously may be used to estimate the reward at each state s after taking an action a.

A state-action value function Q(s, a) may be estimated that determines the optimal action a to take in a state s using the Q-learning technique. The Q-function may be approximated in some embodiments using a DQN architecture such as that depicted in FIG. 4. The trained DQN agent (310) takes state s and reward r as input, and outputs an action a. Once the training is complete, the sentences in bag of sentences 308 represent the most important sentences, and the diagnoses in the bag of diagnoses 306 denote the final predicated diagnoses for the clinical narrative. One example of the overall MDP framework for clinical diagnosis inferencing is presented as pseudocode in Algorithm 1, below:

---
Algorithm 1: MDP Framework

Input: clinical narrative C = $S_1, S_2, ..., S_n$
Output: bag-of-diagnoses D (206), bag-of-sentences S (208)
    D = ∅ and S = ∅;
    for each sentence $S_i$ in C do:
        use $S_i$ as query, search in evidence pool (304), get candidate
            diagnosis $D_i$;
        generate state vector v for sentence-diagnosis pair (si, d);
        calculate reward value r;
        Send (v, r) to trained agent (310), and get action value
    $a_1$ and $a_2$ from trained agent; \\ where $a_1$ and $a_2$ denote actions
    for diagnoses and sentences, respectively
        if action == "stop" then break;
        update D according to $a_1$;
        update S according to $a_2$;
    end
    return D, S
---

For each free form clinical note 202 (and more generally, input data), the output is a bag of diagnoses D (306) and a bag-of-sentences S (308). For the training phase, the steps in Algorithm 1 for each clinical narrative may be run for multiple epochs. During the testing stage, each clinical narrative is processed only once in a single epoch.

Figure 5:
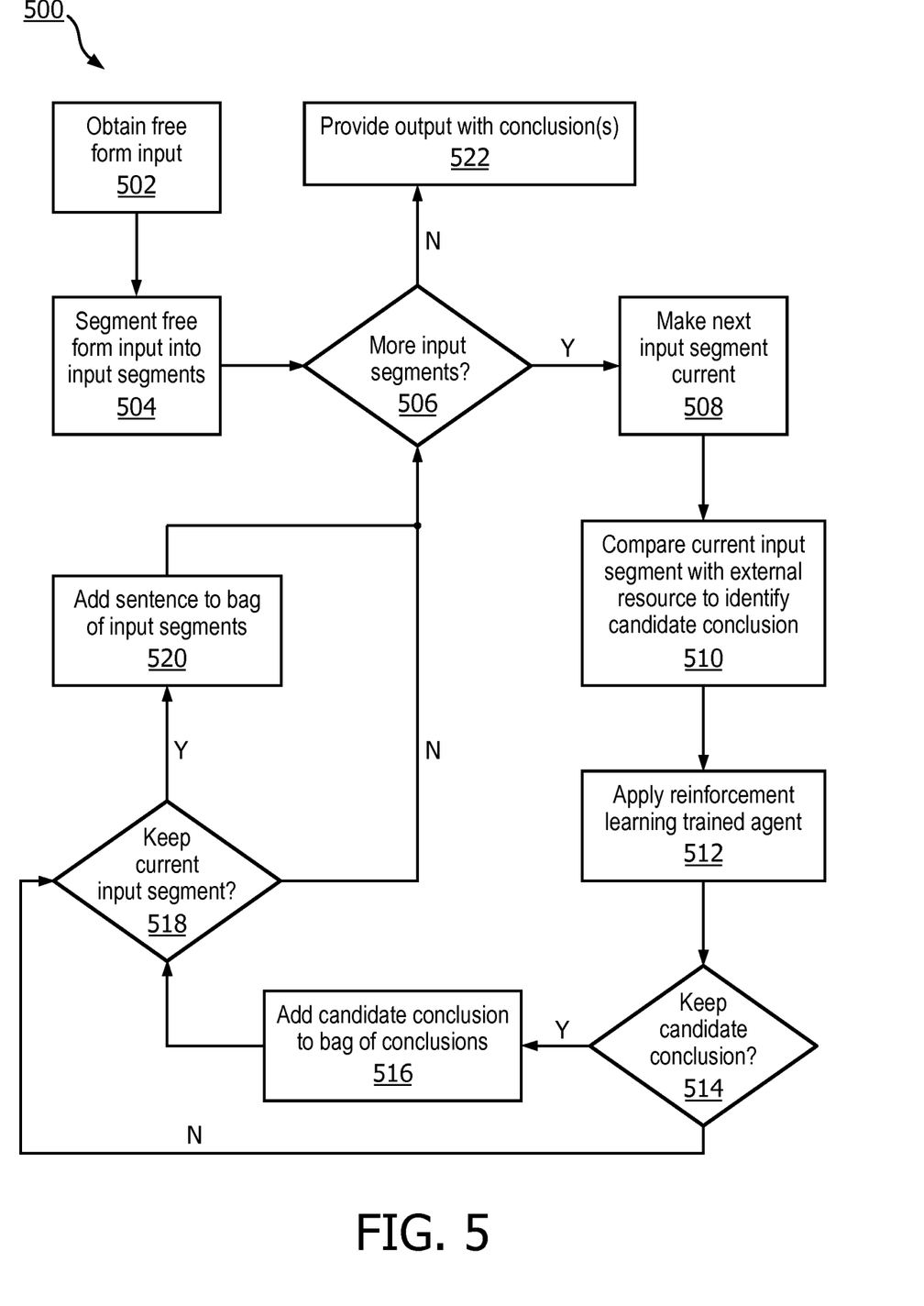
FIG. 5 depicts an example method for practicing selected aspects of the present disclosure.

FIG. 5 depicts an example method 500 for practicing selected aspects of the present disclosure, in accordance with various embodiments. The method 500 may correspond, for example, to the various instructions 161-166 stored in the storage 160 of the system 100. For convenience, the operations of the flow chart are described with reference to a system that performs the operations. This system may include various components of various computer systems, including 100. Moreover, while operations of method 500 are shown in a particular order, this is not meant to be limiting. One or more operations may be reordered, omitted or added.

At block 502, the system may obtain a free form input, e.g., from a hospital information system (e.g., storage 160) or directly from a clinician who composed a free form clinical note. In additional to or instead of the free form clinical notes associated with several examples described herein, other types of free form input are contemplated. For example, free form input containing scientific observations, crime reports, or other observations that yield one or more conclusions may be used as input.

At block 504, the system may, e.g., by way of sentence extraction 206, segment the free form input into a plurality of input segments. With free form clinical notes, this may be done on a sentence-by-sentence basis as described previously. Then, method 500 may enter into a look. At block 506, it may be determined whether there are any more segmented input segments left to analyze. If the answer at block 506 is yes, then method 500 may proceed to block 508.

At block 508, the system may make the next segmented input segment current. At block 510, the current input segment may be compared, e.g., by way of candidate diagnoses searching module 208, with an external resource, such as documents contained in evidence pool 304. Based on this comparison, one or more candidate conclusions (e.g., candidate diagnoses) may be identified. For example, in some embodiments, a title from the best matching document may be taken as the single candidate conclusion. Additionally or alternatively, in some embodiments, any candidate conclusions that satisfy some criterion, such as a confidence threshold, similarity threshold, etc., may be taken as candidate conclusions. As described previously, in some embodiments, one or more of the candidate conclusion(s), the current input segment, and various other data (e.g., similarities S1-5 described previously) may be encoded into a state vector (e.g., 314).

At block 512, the system may, e.g., by way of reinforcement learning and DQN module 212, apply a reinforcement learning trained agent, such as trained agent 310, to the aforementioned state vector. At block 514, the system may determine, based on the application of block 512, whether to keep the candidate conclusion(s). If the answer at block 514 is yes, then at block 516, the candidate conclusion(s) may be added to a bag of conclusions (e.g., bag of diagnoses 306). Then method 500 may proceed to block 518. If the answer at block 514 is so, method 500 may proceed directly to block 518 (or in some cases may skip directly back to block 506).

At block 518, based on the application of block 512, the system may determine whether to keep the current sentence. As discussed previously, at an intuitive level, sentences are kept (e.g., placed in bag of sentences 308) if they are considered "important" to the ultimate inferred diagnosis. For example, if a particular sentence yields a candidate diagnosis that is not rejected, in many cases, and at block 520 of FIG. 5, that sentence may be kept as well. Whether the sentence is kept at block 520 or discarded (i.e., the answer at block 518 is no), method 500 may proceed back to block 506, and the loop may be repeated for the next input segment (e.g., sentence).

This loop may be repeated for a number of increments, e.g., equal to the number of sentences in the input clinical note. Back at block 506, if there are no more segmented input segments to analyze, then method 500 may proceed to block 522. At block 522, the one or more candidate conclusions stored in the bag of conclusions (e.g., bag of diagnoses 306) may be presented to a clinician or patient as audio and/or visual output. In some cases, the input segments contained in the bag of input segments (e.g., bag of sentences 308) may also be provided, e.g., automatically or upon request, so that those input segments that were more influential in inferring the conclusion (diagnosis) can be seen, e.g., as snippets of summary information.

The following example illustrates how techniques described herein may be applied to a free form clinical note to infer a diagnosis. The follow excerpt is the free form clinical note, with a ground truth diagnosis of hypothyroidism:

Description: A 56-year old Caucasian female complains of being markedly more sensitive to the cold than most people. She also gets tired easily, has decreased appetite, and has recently tried home remedies for her constipation. Physical examination reveals hyporeflexia with delayed relaxation of knee and ankle reflexes, and very dry skin. She moves and talks slowly.

During a first iteration, input module 201 may obtain, as a free form clinical note 202, the above-identified excerpt. This may be passed to sentence extraction 206, which in turn may iteratively provide, to candidate diagnoses searching module 208, each sentence. The first sentence, "A 56-year old Caucasian female complains of being markedly more sensitive to the cold than most people," may be matched to a document from evidence pool 304 that includes a diagnosis of triple X syndrome. This sentence/candidate diagnosis pair, $S_i$, $D_i$, is passed to reinforcement learning and DQN module 212 (e.g., to trained agent 310), e.g., in the form of a state 314. Trained agent 310 may be applied to determine that the diagnosis of triple X syndrome should be rejected (i.e., not placed in bag of diagnoses 306). In some embodiments, trained agent 310 may be further applied to reject the first sentence $S_i$ (i.e., not placed in bag of sentences 308), because after all, the corresponding diagnosis was rejected.

During a second iteration, the second sentence $S_2$, "She also gets tired easily, has decreased appetite, and has recently tried home remedies for her constipation," is matched to a candidate diagnosis $D_2$ of co-rectal cancer. Trained agent 310 may determine, e.g., based on a lack of evidence thus far in the free form clinical note, that this diagnosis should be rejected as well. This may also lead to rejection of the sentence $S_2$.

During a third iteration, the third sentence, "Physical examination reveals hyporeflexia with delayed relaxation of knee and ankle reflexes, and very dry skin," may be matched to a candidate diagnosis $D_3$ of hypothyroidism. Because of the evidence accumulated to this point may be strongly suggestive of hypothyroidism, trained agent 310 may accept this candidate diagnosis, which means $D_3$ is added to bag of diagnoses 306. It is also likely that due to the acceptance of the $D_3$, third sentence $S_3$ will be accepted as well, and hence will be stored in bag of sentences 308.

During a fourth iteration, the last sentence $S_4$, "She moves and talks slowly," may be matched to a candidate diagnosis $D_4$ of conjugate gaze palsy. Because the evidence amassed during the multiple iterations does not generally support this diagnosis $D_4$, it may be rejected, along with the sentence $S_4$. There are no more sentences to analyze. Consequently, the diagnosis of hypothyroidism contained in the bag of diagnoses 306 is selected as the inferred diagnosis, and may be output for presentation to a clinician, e.g., on a display and/or audibly.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A method implemented by one or more processors and comprising:
   segmenting a free form clinical notes into a plurality of segments;
   for each segment of the plurality of segments:
      identifying a candidate diagnosis, comprising identifying a document in an evidence pool that most closely matches said segment, the evidence pool comprising clinical reference documents and associated diagnoses, and selecting a diagnosis associated with the identified document as the candidate diagnosis;
      applying a reinforcement learning trained agent to a state vector encoding said segment and said candidate diagnosis to make a determination of whether to accept or reject the candidate diagnosis, the reinforcement learning trained agent being trained to accept or reject candidate diagnoses based on a reward function measuring an accuracy of candidate diagnoses, and wherein the reinforcement learning trained agent is a deep Q-network ("DQN") agent trained via Q-learning to accept or reject candidate diagnoses based on a reward function using a training set of clinical narratives and associated ground truths; and
   presenting the one or more accepted candidate diagnoses;
   wherein the reward function includes an instant reward and a global reward, the instant reward based on a match of the candidate diagnosis with a gold standard diagnosis, and the global reward comprising a number of correct diagnoses accepted so far minus a number of incorrect diagnoses accepted so far.

2. The method of claim 1, wherein identifying said document comprises formulating a query for the evidence pool based on said segment and searching the evidence pool using said query to identify said document.

3. The method of claim 1, wherein the reinforcement learning trained agent further determines whether to accept or reject said segment.

4. The method of claim 1, wherein the state vector comprises a vector representation of words of said segment produced using a Long Short Term Memory Network and mean pooling.

5. The method of claim 3, wherein the state vector comprises one or more of a similarity between said segment and segments accepted so far, a similarity between said segment and a context of the free form clinical note, a similarity between said segment and a context of a clinical reference document associated with the candidate diagnosis, a similarity between segments accepted so far and the context of the clinical reference document associated with the candidate diagnosis, and a similarity between the candidate diagnosis and candidate diagnoses accepted so far.

6. At least one non-transitory computer-readable medium comprising instructions that, in response to execution of the instructions by one or more processors, cause the one or more processors to perform the following operations:
   segmenting a free form clinical note into a plurality of segments;
   for each segment of the plurality of segments:
      identifying a candidate diagnosis, comprising identifying a document in an evidence pool that most closely matches said segment, the evidence pool comprising clinical reference documents and associated diagnoses, and selecting a diagnosis associated with the identified document as the candidate diagnosis;
      applying a reinforcement learning trained agent to a state vector encoding said segment and said candidate diagnosis to make a determination of whether to accept or reject the candidate conclusion diagnosis, the reinforcement learning trained agent being trained to accept or reject candidate diagnoses based on a reward function measuring an accuracy of candidate diagnoses, and wherein the reinforcement learning trained agent is a deep Q-network ("DQN") agent trained via Q-learning to accept or reject candidate diagnoses based on a reward function using a training set of clinical narratives and associated ground truths; and
   presenting the one or more accepted candidate diagnoses;
   wherein the reward function includes an instant reward and a global reward, the instant reward based on a match of the candidate diagnosis with a gold standard diagnosis, and the global reward comprising a number of correct diagnoses accepted so far minus a number of incorrect diagnoses accepted so far.

7. A system comprising one or more processors and memory operably coupled with the one or more processors, wherein the memory stores instructions that, in response to execution of the instructions by one or more processors, cause the one or more processors to perform the following operations:
  segmenting a free form clinical note into a plurality of segments;
  for each segment of the plurality of segments:
    identifying a candidate diagnosis, comprising identifying a document in an evidence pool that most closely matches said segment, the evidence pool comprising clinical reference documents and associated diagnoses, and selecting a diagnosis associated with the identified document as the candidate diagnosis;
    applying a reinforcement learning trained agent to a state vector encoding said segment and said candidate diagnosis to make a determination of whether to accept or reject the candidate diagnosis, the reinforcement learning trained agent being trained to accept or reject candidate diagnoses based on a reward function measuring an accuracy of candidate diagnoses, and wherein the reinforcement learning trained agent is a deep Q-network ("DQN") agent trained via Q-learning to accept or reject candidate diagnoses based on a reward function using a training set of clinical narratives and associated ground truths; and
  presenting the one or more accepted candidate diagnoses;
wherein the reward function includes an instant reward and a global reward, the instant reward based on a match of the candidate diagnosis with a gold standard diagnosis, and the global reward comprising a number of correct diagnoses accepted so far minus a number of incorrect diagnoses accepted so far.

* * * * *